United States Patent
Dennis et al.

(10) Patent No.: US 6,325,828 B1
(45) Date of Patent: Dec. 4, 2001

(54) APPARATUS FOR KNEE PROSTHESIS

(75) Inventors: Douglas A. Dennis, Denver; Richard D. Komistek, Highlands Ranch, both of CO (US)

(73) Assignee: Rose Biomedical Research, Denver, CO (US)

(*) Notice: Subject to any disclaimer, the term of this patent is extended or adjusted under 35 U.S.C. 154(b) by 0 days.

(21) Appl. No.: 08/982,363

(22) Filed: Dec. 2, 1997

(51) Int. Cl.$^7$ .................................................. A61F 2/38
(52) U.S. Cl. ............................ 623/20.14; 623/20.21; 623/20.27; 623/20.28; 623/20.31
(58) Field of Search ........................ 623/16, 18, 20, 623/20.14, 20.21, 20.27, 20.28, 20.29, 20.31

(56) References Cited

U.S. PATENT DOCUMENTS

| | | | |
|---|---|---|---|
| 4,224,697 | * 9/1980 | Murray et al. | 623/20 |
| 4,298,992 | * 11/1981 | Burstein et al. | 623/20 |
| 4,634,444 | * 1/1987 | Noiles | 623/20 |
| 4,888,021 | * 12/1989 | Forte et al. | 623/20 |
| 5,007,933 | * 4/1991 | Sidebotham et al. | 623/20 |
| 5,147,405 | * 9/1992 | Van Zile et al. | 623/20 |
| 5,330,534 | * 7/1994 | Herrington et al. | 623/20 |
| 5,370,699 | * 12/1994 | Hood et al. | 623/20 |
| 5,702,458 | * 12/1997 | Burstein et al. | 623/20 |
| 5,824,100 | * 10/1998 | Kester et al. | 623/20 |
| 5,879,392 | * 3/1999 | McMinn | 623/20 |
| 5,906,643 | * 5/1999 | Walker | 623/20 |

* cited by examiner

Primary Examiner—Corrine McDermott
Assistant Examiner—Choon P. Koh
(74) Attorney, Agent, or Firm—Gibson, Dunn & Crutcher LLP

(57) ABSTRACT

A knee prosthesis which more accurately reproduces the rollback of natural knee movement and, thus, reduces wear on the tibial component. The knee prosthesis includes a femoral component with two cams, the first located between the posterior condylar sections and the second located towards the anterior end of the condylar sections with a slot surface therebetween. The tibial component includes a spine which engages each cam as it rotates along the femoral component and the slot surface during flexion and extension.

8 Claims, 3 Drawing Sheets

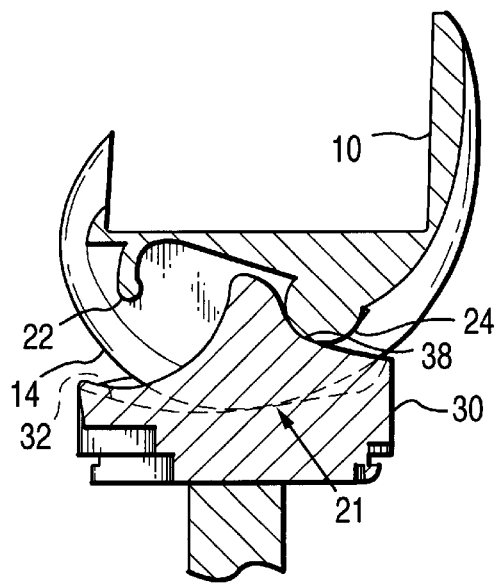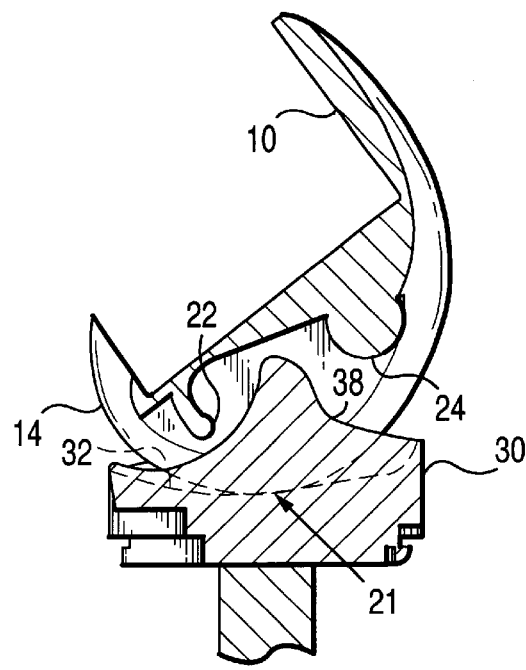
FIG.6A  FIG.6B
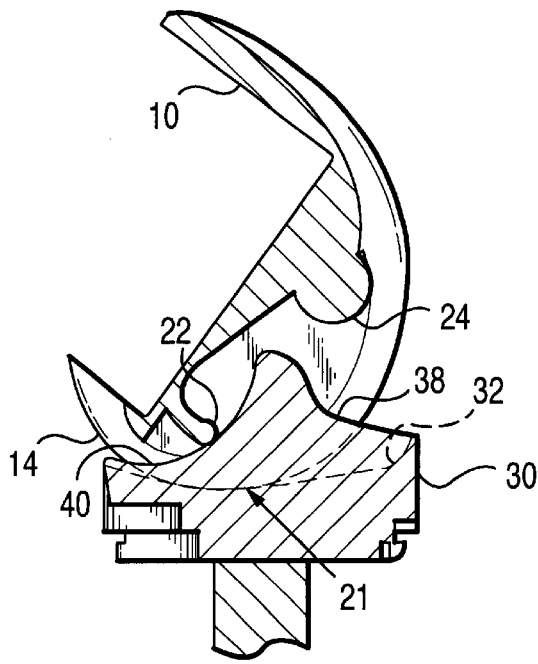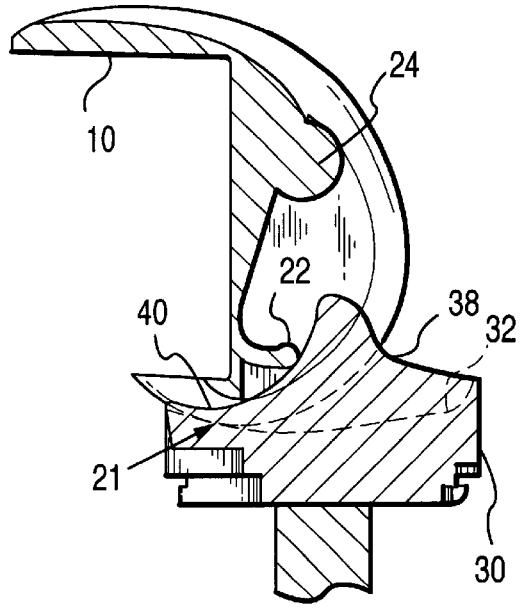
FIG.6C  FIG.6D

APPARATUS FOR KNEE PROSTHESIS

FIELD OF THE INVENTION

The present invention relates to a knee prosthesis. More particularly, it relates to an apparatus and method for engaging the knee prothesis femoral condyles with the tibial component in a manner which simulates natural rollback during flexion and extension, by utilizing a spine on the tibial component which engages a pair of transverse cams extending between the condyles of the femoral component.

BACKGROUND OF THE INVENTION

Prostheses for knee replacement have been developed to try to recreate the natural movement of a knee which has deteriorated due to injury or disease. The complex movement of the knee presents a great challenge to the inventor. Historically, knee prostheses have tried to address these different aspects of knee movement but usually to the detriment of one function or another. This difficulty in recreating natural knee movement is apparent from a description of relevant knee structure.

The knee is a joint between the lower part of the femur which is the upper bone of the leg, and the upper part of the tibia which is the lower bone of the leg. The lower part of the femur is rounded and offset from the longitudinal axes of the straight portion of the femur. The rounded end of the femur has two knuckle like protrusions called condyles. Fluoroscopic research has shown that the femoral condyles of the normal knee contact the tibia anterior to the midline of the saggital plane at knee full extension. As the knee flexes, both condyles move in a posterior direction. The lateral condyle however, moves much more posterior than the medial condyle. At full extension the lateral condyle contacts the tibia approximately 5 to 10 mm anterior. The medial condyle contacts the tibia from 0 to 3 mm anterior at full extension. As the knee bends, the lateral condyle rolls back to a position of 10 to 15 mm posterior at 120 degrees of knee flexion. The medial condyle however, moves back only 4 to 5 mm to a final position of 1 to 3 mm posterior. Therefore, since the lateral condyle is moving more posterior than the medial condyle, screwhome motion is allowed to occur. Screwhome motion is the relative rotation of the lateral condyle with respect to the medial condyle. In the normal knee, research has shown up to 15 degrees of screwhome motion during a deep knee bend. Research on the normal knee has also shown that the lateral condyle rolls back 10 to 15 mm during a deep knee bend.

This relative movement between the femoral condyles and the tibia is due in part to the fact that the condyles are offset from the longitudinal axis of the femur. However, that is not the only reason. This complex combination of rolling and sliding is defined by not only the configuration of the respective surfaces of the femur condyles and the tibia, but also by the structure of connecting tendons, ligaments and tissue. These connecting elements are partially or entirely removed in typical prostheses installations.

Further complicating the movement is the torsional effect previously mentioned, whereby the tibia turns about its longitudinal axis as it flexes or extends. It is well known that the tibia rotates outward (that is, the right tibia rotates clockwise and the left tibia rotates counterclockwise, as viewed from above) as the tibia extends. This produces a flaring out of the feet during extension and the reverse during flexion. This effect is a result of complex interaction at the knee joint. The absence of this effect in a prosthesis may produce discomfort and awkwardness in walking.

In summary, knee prostheses should replicate the range of movement of the knee from full extension to full flexion and back to extension again while recreating the simultaneous posterior rollback of the femoral condyles on the tibia during flexion as well as torsional movement. Several prostheses have been developed which attempt to recreate the natural shape and movement of the knee. These condylar prostheses, so named because they attempt to replicate the shape of the femoral condyles, have two components. The femoral component recreates the condylar shape of the lower femur with one end forming a groove in which the patella glides. The tibial component has recessed surfaces to receive the condylar portions of the femoral component. The tibial component also may have a spine protruding upwards into a slot in the femoral component which guides and restricts the range of movement of the joint through flexion and extension.

A successful example of a condylar prosthesis is disclosed in U.S. Pat. No. 4,298,992 granted to Burstein et al. That invention included a slot in the femoral component which engages the spine of the tibial component during flexion to recreate posterior femoral rollback. The slot in the Burstein et al. invention engages the spine at a point that is quite high on the spine. The resulting pressures on such a small point of contact require a large spine and sufficient bone resection to accommodate it.

The prostheses disclosed in U.S. Pat. Nos. 4,888,021 and 5,011,496 both granted to Forte et al. contain a spine on the tibial component which is shaped to provide a large contact surface area with the femoral component. The intent is to enlarge the area of contact between the components to reduce the wear resulting from high pressures on small areas of contact. The invention also provides for a separate patellar component intended to fit within the patellar groove portion of the femoral component.

U.S. Pat. No. 5,549,686 granted to Johnson et al. sought to improve upon the prior art by locating a tapered cam on the femoral component between and towards the posterior end of the condyles, that is, away from the end forming the patellar groove. The cam engages the spine of the tibial component at a lower point on the spine, thereby requiring a smaller spine and allowing for greater resistance to pressures because the spine is thicker towards its base. This configuration reduces the amount of bone to be resected.

Other knee prostheses are disclosed in U.S. Pat. No. 4,892,547 granted to Brown; U.S. Pat. No. 4,959,071 granted to Brown et al.; U.S. Pat. No. 5,219,362 granted to Tuke et al. and U.S. Pat No. 5,330,534 granted to Herrington et al.

Each of these developments in the prior art relies upon the sliding of the tibial component across the femoral component to reproduce the movement of the knee. While the femoral and tibial component engagements are designed to recreate posterior femoral rollback and to restrain the range of movement of the joint, they fail in accurately mimicking the natural movement of the knee joint for a variety of reasons. One strong reason is that they fail to emulate natural torsional movement. Over an extended time this may result in excessive wear on the components, as well as poor utility for the patient. Degradation of the component and the joint results in great discomfort and increasing disability. Ultimately, the prosthetic components may fail, necessitating expensive and intrusive revision or replacement surgery on the joint. Replacement of the prosthetic components require additional preparation of the remaining bone of the joint and repeat fixation of the prosthesis to the bone. The additional work on remaining bone structure may result in less effective bonding of the component and, thus, a weakening of the joint. Fluoroscopic research has shown that during a deep knee bend prior art protheses do not replicate normal posterior femoral rollback. Since the cam and post do not contact during gait, fluoroscopic studies have shown that such prostheses do not replicate normal knee motion. In fact, sliding often occurs.

SUMMARY OF THE INVENTION

The present invention is a method and apparatus for more accurately reproducing the posterior rollback of natural knee movement and, thus, reducing wear on the tibial plastic component and producing greater comfort and utility. The femoral component of the prosthesis includes a pair of condyles of conventional design, joined by a patellar groove and separated by a slot. The slot is defined by the condyles on either side and a slot surface therebetween at the bottom of the slot. Extending between the lateral and medial condyles, through the slot and integral with the slot bottom, are a pair of transverse cams.

The tibial component of the prosthesis includes a bearing surface to receive the bearing surfaces of the condyles of the mating femoral component. The tibial component also includes a protruding spine having depressions posteriorly and anteriorly with a protrusion therebetween. The posterior depression of the tibial component receives the posterior cam of the femoral component when the prosthesis is toward flexion, and the anterior depression of the tibial component receives the anterior cam of the femoral component when the prosthesis is toward extension. The spine surface interacts with the cams to imitate natural posterior femoral rollback by limiting and defining the pivot between the femoral component posterior post and the tibial component.

BRIEF DESCRIPTION OF THE DRAWING

FIGS. 6A–6D are side cut-away views of the femoral and tibial components of the present invention articulating in approximately 0, 30, 60 and 90° of flexion, respectively.

DETAILED DESCRIPTION OF A PREFERRED EMBODIMENT

Figure 1:
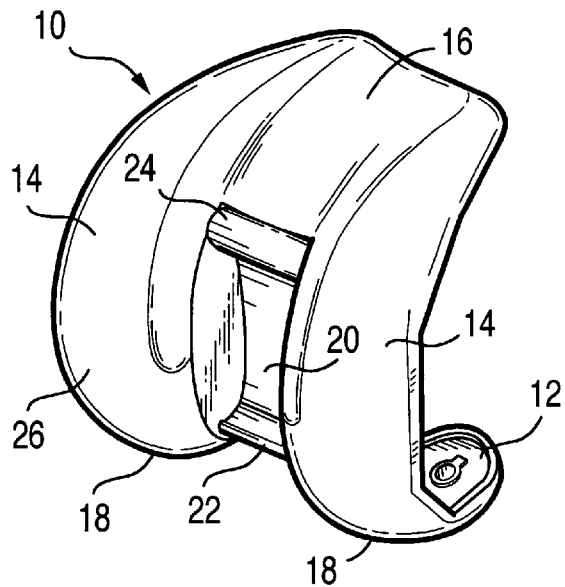
FIG. 1 is a perspective view of the femoral component of the present invention.
Figure 2:
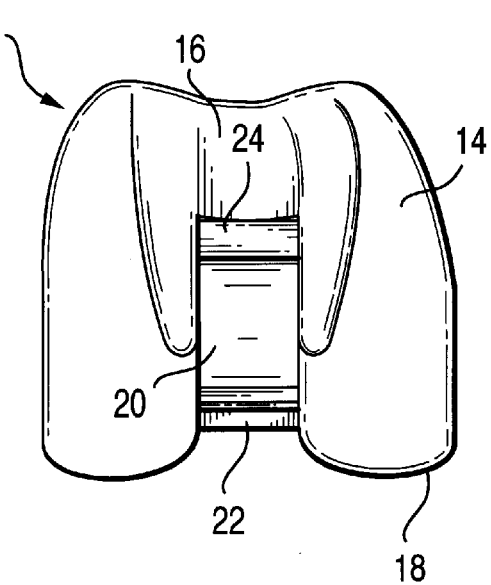
FIG. 2 is a plan view of the femoral component of the present invention.

A perspective and plan view of the preferred embodiment of the femoral component of the invention are depicted in FIGS. 1 and 2, respectively. The femoral component 10 is of an overall size and shape that is typical in the field of condylar knee prostheses. Ingrowth texturing is on the upper surface of portions of the femoral component 10, illustrative texturing 12 being shown in FIG. 1. The femoral component 10 is fabricated in the well-known manner from forged stainless steel or other durable biocompatible material such as titanium or cobalt alloys or alumina or zirconia ceramics. The femoral component 10 includes two condylar protrusions 14 which run the length of each side of the component 10. The condylar sections 14 flatten and merge at one end of the femoral component 10 to create a patellar surface groove 16. The condylar sections 14 protrude more distinctly towards the other end of the femoral component 10, curving sharply at the end 18 to replicate the condyles normally found in the lower femur. The normal size, shape, material and manufacture of the femoral component 10 of condylar knee prostheses are generally known in the art, and are not described in detail herein apart from the aspects important to the present invention.

The femoral component 10 includes a slot 20 running down the middle of the component 10. The slot 20 forms out of the patellar surface 16 of the component 10 and deepens as it runs to the posterior end where the condylar sections 14 are most pronounced. Two cams are located across the slot 20 and between the condylar sections 14 of the femoral component 10. The first cam 22 is located at the extreme posterior end of the condylar sections 14 at the point where those sections curve sharply upwards. The first cam 22 is recessed below the surface level of the condylar sections 14 and is a part of and protrudes out of the surface of the slot 20. The second cam 24 is located near the midpoint of the femoral component 10 towards the anterior end of the condylar sections 14 where the surface of those sections begins to form the bottom horizontal plane 26 of the femoral component 10. The second cam 24 is recessed below the surface level of the condylar sections 14 and is a part of and protrudes out of the surface of the slot 20.

Figure 3:
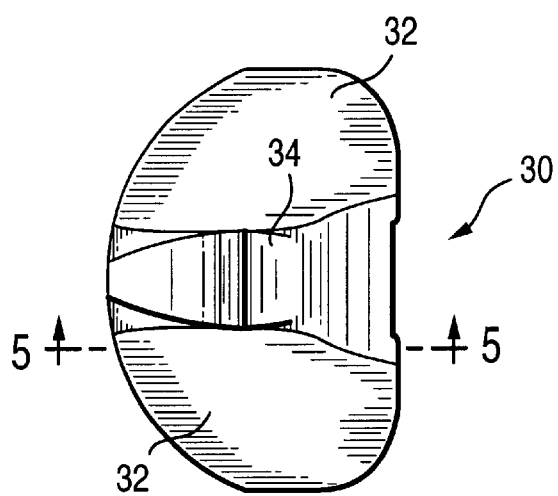
FIG. 3 is a plan view of the tibial component of the present invention.
Figure 4:
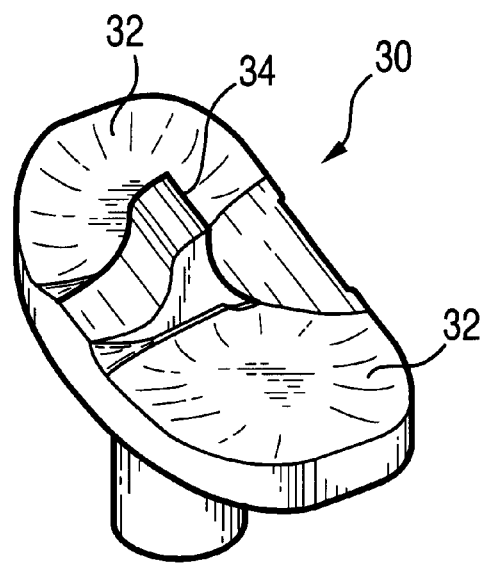
FIG. 4 is a perspective view of the tibial component of the present invention.

A plan and perspective view of the preferred embodiment of the tibial component of the invention are depicted in FIGS. 3 and 4, respectively. The tibial component 30 is of an overall size and shape that is typical in the field of condylar knee prostheses. The tibial component 30 is preferably fabricated from a biocompatible material having a low coefficient of friction, such as polyethylene or other polymers or composites of the same, in order to allow smooth interaction between the tibial component 30 and the femoral component 10. The tibial component 30 includes recessed surfaces 32 designed to receive the protruding condylar sections 14 of the femoral component 10.

Figure 5:
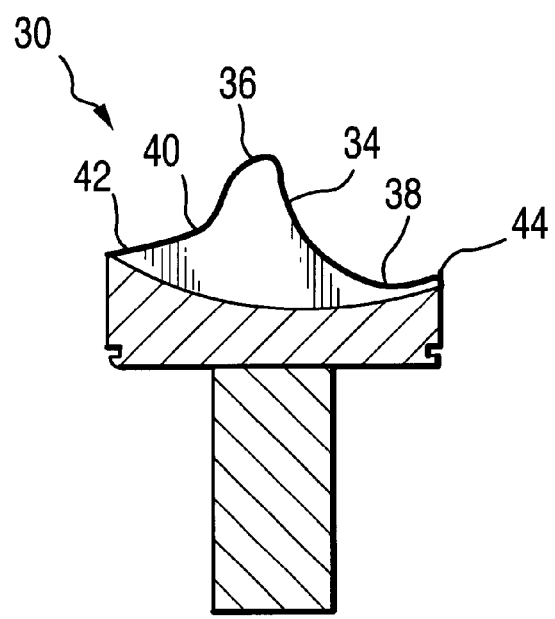
FIG. 5 is a side sectional view of the tibial component of the present invention along line 5—5 of FIG. 3.

A spine 34 rises from the tibial component 30 between recessed surfaces 32, and extends generally in the anterior-posterior direction as best shown in the sectional views of FIG. 5 taken along line 5—5 of FIG. 3 to show the lateral side of cam 34. Cam 34 includes lateral upper cam surface 36 dividing anterior trough 38 from posterior trough 40. Posterior trough 40 is defined at the posterior end by posterior bump 42, and anterior trough 38 is defined at the anterior end by anterior bump 44.

The engagement between the femoral component 10 and tibial component 30 is shown in FIGS. 6A, 6B, 6C and 6D at 0°, 30°, 60° and 90°, respectively. Together, the drawings serve to illustrate the interaction of the components from full flexion to full extension and, in particular, to illustrate that the point of contact between the femoral condyles 14 and tibial component recessed bearing surfaces 32 moves posteriorly during flexion to mimic actual knee movement.

At 0° flexion, that is, full extension (FIG. 6A), it can be seen that the femoral component 10 anterior cam 24 is fully engaged with the anterior trough 38 of the tibial component 30. The point of contact 21 between the femoral condyles 14 and the recessed surfaces 32 of the tibial component 30 is now approximately 7 mm anterior from the centerline of the tibial component 30.

At 30° flexion (FIG. 6B), it can be seen that the engagement between the femoral component 14 and the tibial component 30 is defined by the femoral condyles 14 and the recessed surfaces 22 of the tibial component 3D. The cams 24 and 22 of the femoral component 10 are not engaged with the spine 34, the anterior cam 24 having separated from the anterior trough 38 at approximately 20° flexion. The point of contact 21 is approximately the centerline of the tibial component 30.

At 60° flexion (FIG. 6C), it can be seen that the surface of the posterior cam 22 of the femoral component 10 has impinged upon the posterior trough 40 of the tibial component 30. The impingement first occurs at approximately 50° flexion. As flexion continues, the femoral component 10 is caused to slide on the tibial component 30 as evidenced in FIG. 8C. The point of contact 21 between the femoral condyles 14 and the recessed bearing surfaces 32 of the tibial component 30 is now approximately 5 mm posterior from a centerline of the tibial component 30.

At 90° flexion (FIG. 6D), it can be seen that the point of contact between the femoral condyles 14 and the tibial recessed bearing surfaces 32 is approximately 8 mm posterior from a centerline of the tibial component 30. At that degree of flexion, the femoral component posterior cam 22 is still fully engaged with the tibial posterior trough 40. The relative movement of the femoral component 10 in relation to the tibial component 30 is essentially rotation and sliding between the femoral component posterior cam 22 and the tibial component posterior trough 40.

The spine 34 of the tibial component 30 thus engages the posterior cam 22 and anterior cam 24 of the femoral component 10 in a manner that produces a sliding of the femoral component 10 in relation to the tibial component 30. The anterior cam 24 and posterior cam 22 act as steps to limit the extent of anterior-posterior movement while simultaneously producing desired rollback. This emulates the movement of a natural knee joint.

It can be appreciated that the surfaces of the spine 34 and/or the cams 24 and 22 can be made asymmetrical, so that a torsional movement is produced as the femoral component 10 and tibial component 30 produce flexion and extension. For example, the surface of the spine 34 may slope downward from the lateral surface to the medial surface. The patient's body weight urging the femoral component 10 toward the tibial component 30 thus would twist the tibial component 30 to produce a stable line of contact between the tibial component 30 recessed bearing surfaces 32 and femoral condyles 14. This twisting, or torsional movement, could be furthered when the femoral component anterior post 24 engages the sloping surface of the tibial component 30 anterior trough 38.

The degree of torsional movement is easily controlled by the slope in the engaging surfaces; a higher slope will produce greater torsional rotation. It should also be appreciated that, while the preferred embodiment described above employs an asymmetrical spine 34 on the tibial component 30 the same effect could be achieved with an asymmetrical femoral component employing sloping cams 22 and 24 or there could be asymmetry on both the femoral component 10 and tibial component 30.

What is claimed:

1. A knee prosthesis, comprising:
    a femoral component attachable to a femur, the femoral component having a pair of substantially parallel condyles with a slot therebetween, a first cam extending between the condyles and through the slot toward an anterior end of the femoral component, and a second cam extending between the condyles and through the slot toward a posterior end of the femoral component, the condyles, first cam and second cam thereby defining a space bounded by the condyles on each side, by the first cam toward the anterior end of the femoral component, and by the second cam toward the posterior end of the femoral component; and
    a tibial component attachable to a tibia, the tibial component being rotatably and slidably engaged with a femoral component and having two bearing surfaces to receive the femoral component condyles, the bearing surfaces separated by a spine protruding from the bearing surfaces and engageable with the first cam and second cam;
    wherein the first cam, condyles and bearing surfaces are configured such that the spine contacts the fist cam at full extension of the prosthesis, and the spine contacts the second cam at fill flexion of the prosthesis and being further configured such that the spine contacts the first cam from throughout the range of at least 0° to 10° flexion.

2. The knee prosthesis of claim 1, where the spine contacts the first cam throughout the range of at least 0–20° flexion.

3. The prosthesis of claim 1, wherein the first cam, second cam, condyles and bearing surfaces are configured such that the spine contacts the second cam at 90° flexion.

4. The prosthesis of claim 1, wherein the first cam, second cam, condyles and bearing surfaces are configured such that the spine contacts the second cam from approximately 50° to 90° flexion.

5. The prosthesis of claim 1, wherein the spine includes an anterior surface for engagement with the first cam and a posterior surface for engagement with the second cam.

6. The prosthesis of claim 1, wherein the first cam, second cam, condyles and bearing surfaces are configured to define a point of contact between the condyles and the bearing surfaces, whereby the point of contact moves in a posterior direction during flexion.

7. A knee prosthesis, comprising:
    a femoral component attachable to a femur, the femoral component having a pair of substantially parallel condyles with a slot therebetween, a first cam extending between the condyles and through the slot toward an anterior end of the femoral component, and a second cam extending between the condyles and through the slot toward a posterior end of the femoral component, the condyles, first cam and second cam thereby defining a space bounded by the condyles on each side, by the first cam toward the anterior end of the femoral component, and by the second cam toward the posterior end of the femoral component; and
    a tibial component attachable to a tibia, the tibial component being rotatably and slidably engaged with a femoral component and having two bearing surfaces to receive the femoral component condyles, the bearing surfaces separated by a spine protruding from the bearing surfaces and engageable with the first cam and second cam;
    wherein the first cam, condyles and bearing surfaces are configured such that the spine contacts the first cam at full extension of the prosthesis, and the spine contacts the second cam at full flexion of the prosthesis; configured to define a point of contact between the condyles and the bearing surfaces whereby the point of contact moves in a posterior direction during flexion, the point of contact at full extension being more than 10 mm anterior to the point of contact at 90° flexion.

8. The prosthesis of claim 7, wherein the point of contact at full extension is approximately 15 mm anterior to the point of contact at 90° flexion.

* * * * *